United States Patent [19]

Dies et al.

[11] Patent Number: 4,490,368

[45] Date of Patent: Dec. 25, 1984

[54] DIURETIC AND ANTIHYPERTENSIVE COMPOSITION COMPRISING XIPAMIDE AND TRIAMTERENE

[75] Inventors: Rainer Dies, Hamburg; Bodo Asmussen, Ammersbeck, both of Fed. Rep. of Germany

[73] Assignee: Beiersdorf Aktiengesellschaft, Fed. Rep. of Germany

[21] Appl. No.: 426,540

[22] Filed: Sep. 29, 1982

[30] Foreign Application Priority Data

Nov. 3, 1981 [DE] Fed. Rep. of Germany ....... 3143471

[51] Int. Cl.$^3$ ............................................. A61K 31/62
[52] U.S. Cl. ..................................... 424/232; 424/251
[58] Field of Search ................................ 424/251, 232

[56] References Cited

U.S. PATENT DOCUMENTS 3,081,230  3/1963  Weinstock et al. ................. 424/251
3,567,777  3/1971  Liebenow ....................... 424/309 X

FOREIGN PATENT DOCUMENTS 2707103  8/1977  Fed. Rep. of Germany ...... 424/251
2936244  3/1980  Fed. Rep. of Germany ...... 424/251

OTHER PUBLICATIONS

Emrhart, et al., (Editors), *Arzneimitter*, vol. 2, Verlag Chemie, Weinheim/Bergstr, 1972, p. 346.
Helwig, et al., *Moderne Arzneimittel*, vol. 5, Wissenschaftliche Verlagsgesellschaft, Stuttgart, 1980, p. 871.
Armam, et al., *Arzneim.-Forsch.*, 33, (1), 131, (1983).
Diembeck, et al., *Arzneim.-Forsch.*, 31, (11), 1482, (1982).
Hokenegger, M., et al., *Int. J. Clin. Pharmacol. Biopharm.*, 1976, 13, (4), 298–303.
*Chemical Abstracts*, 85: 104041k, (1976) [Hohenegger, M., et al., *Int. J. Clin. Pharmacol. Biopharm.* 1976, 13, (4), 298—303].

*Primary Examiner*—Richard A. Schwartz
*Attorney, Agent, or Firm*—Sprung, Horn, Kramer & Woods

[57] ABSTRACT

Pharmaceutical composition containing 1 part by weight of xipamide and 3–4 parts by weight of triamterene, for diuretic and antihypertensive treatment.

7 Claims, No Drawings

DIURETIC AND ANTIHYPERTENSIVE COMPOSITION COMPRISING XIPAMIDE AND TRIAMTERENE

The invention relates to a new pharmaceutical composition, its use and its preparation.

4-Chloro-5-sulphamoyl-salicylic acid 2,6-dimethylanilide is known as xipamide and has been introduced as a diuretic agent, compare U.S. Pat. No. 3,567,777.

2,4,7-Triamino-6-phenyl-pteridine is known as triamterene and is a recognised diuretic agent, compare U.S. Pat. No. 3,081,230.

Xipamide and triamterene have been used in human medicine for many years, on the basis of their diuretic and antihypertensive properties.

A combination of xipamide and triamterene in which the envisaged weight ratios of xipamide to triamterene are 1:0.5, 1:1 or 1:1.5 has also already been disclosed by Hohenegger/Holzer, (Int. J. Clin. Pharmacol. 13 1976, 289–303). In particular, the weight ratio of 1:1 is regarded as being of particular significance (page 302, right-hand column centre), and in contrast the ratio 1:1.5 provides no additional advantage.

It has now been found, surprisingly, that a pharmaceutical composition containing 1 part by weight of xipamide and 3–4 parts by weight of triamterene have exceptionally advantageous pharmacological and toxicological properties.

Xipamide is a saluretic agent having a powerful action of medium-term duration. The diuretic and saluretic action extends over a period of about 16 hours. Its use as a mono-substance leads to hypokaliaemia, which must be regarded as a cause of tiredness, spasms and similar complaints.

Triamterene is a diuretic agent which increases the excretion of sodium and water but decreases the excretion of potassium. If xipamide and triamterene are used, according to the invention, together in a weight ratio of 1:3 to 1:4, triamterene is able to cancel out the kaliuretic effect of xipamide. The use of the composition according to the invention thus permits effective diuretic and antihypertensive treatment over a relatively long period. During the treatment, a satisfactory hydroelectric equilibrium is thereby maintained in the blood. Unexpectedly, the excretion of potassium is not increased during this treatment in confirmed cases of natriuresis and excretion of water. This excellent pharmacological effect could not be deduced from the prior art.

In addition, it has been found, unpredictably, that the toxicity of the mixture according to the invention is lower than that which could be expected on the basis of the toxicity of the constituents. On oral administration to mice, the toxicity of the composition according to the invention is lower than the toxicity of its constituents.

The pharmaceutical composition according to the invention is thus particularly suitable in human medicine in the therapy of oedemas of various origin and of certain forms of adiposity, and, in addition, for the treatment of refractory oedemas, especially in cases of cardiac insufficiency, and in the long-term treatment of arterial hypertonia.

The pharmaceutical compositions according to the invention preferably contain 1 part by weight of xipamide and 3 parts by weight of triamterene. For example, a tablet according to the invention or a dragee contains 10 mg of xipamide, 30 mg of triamterene and 180 mg of excipient.

When administered to adults, the daily dose of the active compounds administered orally can be, for example, about 10 to 30 mg of xipamide with corresponding amounts of triamterene, preferably about 10 mg of xipamide and 30 mg of triamterene up to about 20 mg of xipamide and 60 mg of triamterene.

The pharmaceutical compositions according to the invention can be administered parenterally or through the digestive tract, in which case oral administration is preferred.

These pharmaceutical compositions can be, for example, solid or liquid, and can be in the pharmaceutical forms usually employed in human medicine, for example in the form of tablets, dragees, gel beads, granules, a drinkable suspension, suppositories or an injectable solution, the preparation of which can be effected by conventional processes. The excipients usually employed in these pharmaceutical compositions, for example talc, colloidal silicon dioxide, gum arabic, lactose, starch, magnesium stearates, cacao butter, aqueous or non-aqueous vehicles, fats of animal or vegetable origin, paraffinic derivatives, glycols, various wetting, dispersing or emulsifying agents and/or preservatives, can be added to the active compounds.

The example which follows illustrates the invention, but without limiting it.

PHARMACEUTICAL COMPOSITION

Tablets which correspond to the following formulation are prepared:

| | |
|---|---|
| Xipamide | 10 mg |
| Triamterene | 30 mg |
| Excipient q.s. | 220 mg |

Excipient: Aerosil, maize starch, treated starch, lactose, magnesium stearate and talc.

PHARMACOLOGICAL INVESTIGATION

1. Diuretic activity

The diuretic activity of the new combination according to the invention and of its constituents were investigated in respect of diuresis, natriuresis and kaliuresis on normal hydrated rats.

The diuretic investigations were carried out on female Wistar rats (Ivanovas/Kisslegg (Allg.)), weighing 180–200 g. On the eve of the day of experiment, drinking water was held back from the animals. Standard rat diet (Altromin 1324) was available ad libitum. At the start of the experiment, the animals each received 5 ml of 0.3 percent sodium chloride solution, by stomach tube, for hydration. After peroral administration of the test substances, the animals were kept in stainless steel metabolism cages in an air-conditioned room at $22 \pm 1°$ C. and at about 65% relative atmospheric humidity.

The urine was collected for 6 hours in potassium-free containers. Xipamide, triamterene and the combination were administered in each case to 25 animals in doses of 0.1 mg/kg (xipamide) and 0.3 mg/kg (triamterene) and in the combination of these doses. The electrolytes sodium and potassium excreted were determined by flame photometry using a BECKMANN spectrophotometer. The results are given in Table 1.

TABLE 1

Summary of the urine and electrolyte excretion following administration of xipamide and triamterene and the combination ($\bar{x} \pm 2s\ \bar{x}$). Dose ratio 1:3.

| | Vol. ml/kg/ 6 hours | Δ % | Na.+ mmols/ kg/ 6 hours | Δ % | K+ mmols/ kg/ 6 hours | Δ % |
|---|---|---|---|---|---|---|
| no treatment | 24.3 ±3.8 | | 1.00 ±0.3 | | 1.60 ±0.3 | |
| xipamide 1.0 mg/kg | 47.4 ±3.4 | ±95.1 | 2.7 ±0.3 | +170 | 2.7 ±0.3 | +69 |
| triamterene 3.0 mg/kg | 20.5 ±2.4 | −15.6 | 1.0 ±0.2 | ±0 | 0.9 ±0.2 | −44 |
| xipamide/ triamterene 1.0/3.0 mg/kg | 50.3 ±3.4 | +107 | 3.7 ±0.3 | +270 | 0.7 ±0.2 | −56 |

The above table shows that the new combination according to the invention ensures an excellent activity in the field of diuresis and natriuresis, it also being very remarkable that this diuresis and natriuresis are accompanied by a large saving in the excretion of potassium, since this excretion is unexpectedly much lower than could be expected on the basis of the constituents.

2. Determination of the acute toxicity on oral administration to mice

The acute toxicity was determined on groups of 10 male, non-hydrated mice weighing about 20 g.

The compounds were administered orally in 0.5% methylcellulose mucous by means of an oesophagus tube.

Xipamide and triamterene were administered separately and as a mixture. The following lethalities were determined:

2.1 Xipamide

| Dose mg/kg of BW* | Lethality |
|---|---|
| 0 | 0/10 |
| 631 | 2/10 |
| 1,000 | 6/10 |
| LD$_{50}$ (95% confidence range) 877 mg/kg | |

*BW = body weight

2.2 Triamterene

| Dose mg/kg of BW | Lethality |
|---|---|
| 0 | 0/10 |
| 500 | 3/10 |
| 2,000 | 6/10 |
| LD$_{50}$ (95% confidence range) 1,725 mg/kg | |

2.3 Combination

Non-hydrated C.D. mice were used for determining the toxicity of the combination. The following lethalities were recorded:

| Xipamide (mg/kg) | Triamterene (500 mg/kg) |
|---|---|
| 0 | 3/10 |
| 1,500 | value lower than the sum of the individual values |

We claim:

1. Pharmaceutical composition for diuretic and antihypertensive use containing 1 part by weight of xipamide and 3-4 parts by weight of triamterene.

2. Pharmaceutical composition according to claim 1, containing 1 part by weight of xipamide and 3 parts by weight of triamterene.

3. Pharmaceutical composition according to one of claims 1 or 2, containing pharmaceutical carrier substances suitable for oral administration.

4. Pharmaceutical composition according to one of claims 1-3 in the form of tablets or dragees containing 10 mg of xipamide and 30 mg of triamterene.

5. A method for diuretic and antihypertensive treatment which comprises administering to a host a diuretic and/or antihypertensive effective amount of a pharmaceutical composition according to one of claims 1-4.

6. A method according to claim 5 in which the active compound is administered orally.

7. A method according to claim 5 in which the active compound is administered parenterally.

* * * * *